(12) United States Patent
Niu et al.

(10) Patent No.: US 9,610,151 B2
(45) Date of Patent: Apr. 4, 2017

(54) METHODS OF USING COMPRESSIBLE TUBES FOR PLACING IMPLANTS

(71) Applicant: MiMedx Group, Inc., Marietta, GA (US)

(72) Inventors: Mei Niu, Shanghai (CN); Daniel Hernandez, Wesley Chapel, FL (US); Thomas J. Koob, Tampa, FL (US)

(73) Assignee: MiMedx Group, Inc., Marietta, GA (US)

( * ) Notice: Subject to any disclaimer, the term of this patent is extended or adjusted under 35 U.S.C. 154(b) by 16 days.

(21) Appl. No.: 14/644,739

(22) Filed: Mar. 11, 2015

(65) Prior Publication Data

US 2015/0196384 A1    Jul. 16, 2015

Related U.S. Application Data

(62) Division of application No. 13/105,353, filed on May 11, 2011, now Pat. No. 9,005,285.

(Continued)

(51) Int. Cl.
*A61F 2/08* (2006.01)
*A61L 27/36* (2006.01)
(Continued)

(52) U.S. Cl.
CPC ........... *A61F 2/0805* (2013.01); *A61B 17/06* (2013.01); *A61B 17/06004* (2013.01); *A61B 17/06066* (2013.01); *A61B 17/06166* (2013.01); *A61B 17/1146* (2013.01); *A61B 17/3468* (2013.01); *A61B 2017/00336* (2013.01); *A61B 2017/00902* (2013.01); *A61B 2017/00942* (2013.01);
(Continued)

(58) Field of Classification Search
CPC .............. A61B 17/06; A61B 17/06004; A61B 2017/060562; A61B 2017/06028; A61B 2017/06047; A61F 2/0805
See application file for complete search history.

(56) References Cited

U.S. PATENT DOCUMENTS 2,748,774 A * 6/1956 Novak ..................... A61L 17/08
28/165
3,212,502 A * 10/1965 Myers ..................... A61B 17/06
24/706

(Continued)

FOREIGN PATENT DOCUMENTS

| EP | 0478949 | 4/1992 | |
| FR | 2743294 A1 * | 7/1997 | ............... A61F 2/08 |
| WO | WO2012/121986 | 3/2012 | |

OTHER PUBLICATIONS

Arthrex® Partial Brochure, The Next Generation in Hand, Wrist and Elbow Repair Technology, pp. 2, 4, 11, 15, 17, 19 and 20, © 2008.
(Continued)

*Primary Examiner* — Andrew Iwamaye
(74) *Attorney, Agent, or Firm* — Myers Bigel, P.A.

(57) ABSTRACT

Medical delivery devices include a needle and a flexible compressible impermeable tube attached to the needle. The compressible tube has an open interior channel. The device is adapted to releasably hold a length of a medical implant in the open interior channel of the tube. The medical implant can be slidably inserted into the interior channel of the tube and is loosely held by the tube.

24 Claims, 9 Drawing Sheets

Related U.S. Application Data

(60) Provisional application No. 61/345,292, filed on May 17, 2010.

(51) Int. Cl.

| | |
|---|---|
| A61L 27/24 | (2006.01) |
| A61B 17/06 | (2006.01) |
| A61B 17/00 | (2006.01) |
| A61F 2/82 | (2013.01) |
| A61B 17/11 | (2006.01) |
| A61B 17/34 | (2006.01) |

(52) U.S. Cl.
CPC ............... *A61B 2017/06052* (2013.01); *A61F 2002/825* (2013.01); *A61L 27/24* (2013.01); *A61L 27/3666* (2013.01)

(56) References Cited

U.S. PATENT DOCUMENTS

| | | | |
|---|---|---|---|
| 4,050,100 A | 9/1977 | Barry | |
| 4,265,246 A | 5/1981 | Barry | |
| 4,805,292 A | 2/1989 | Noguchi | |
| 4,901,722 A | 2/1990 | Noguchi | |
| 5,102,418 A | 4/1992 | Granger et al. | |
| 5,116,358 A | 5/1992 | Granger | |
| 5,123,911 A | 6/1992 | Granger et al. | |
| 5,152,769 A | 10/1992 | Baber | |
| 5,259,845 A | 11/1993 | Korthoff | |
| 5,280,674 A | 1/1994 | Granger et al. | |
| 5,306,288 A | 4/1994 | Granger et al. | |
| 5,378,469 A | 1/1995 | Kemp et al. | |
| 5,382,257 A * | 1/1995 | Lewis | A61B 17/0401 606/148 |
| 6,059,800 A | 5/2000 | Hart et al. | |
| 6,342,060 B1 * | 1/2002 | Adams | A61B 17/1146 606/151 |
| 6,500,184 B1 * | 12/2002 | Chan | A61B 17/0482 606/144 |
| 6,565,960 B2 | 5/2003 | Koob et al. | |
| 6,821,530 B2 | 11/2004 | Koob et al. | |
| 7,585,311 B2 | 9/2009 | Green et al. | |
| 7,901,455 B2 | 3/2011 | Koob et al. | |
| 8,100,942 B1 | 1/2012 | Green et al. | |
| 8,109,969 B1 | 2/2012 | Green et al. | |
| 2003/0167090 A1 * | 9/2003 | Chervitz | A61F 2/0805 623/13.14 |
| 2005/0033362 A1 | 2/2005 | Grafton | |
| 2005/0192631 A1 | 9/2005 | Grafton | |
| 2006/0058890 A1 | 3/2006 | Lesh | |
| 2007/0098755 A1 * | 5/2007 | Patel | A61F 2/0059 424/423 |
| 2008/0161917 A1 | 7/2008 | Koob et al. | |
| 2008/0188933 A1 | 8/2008 | Koob et al. | |
| 2008/0200992 A1 * | 8/2008 | Koob | A61F 2/08 623/23.72 |
| 2009/0287308 A1 | 11/2009 | Davis et al. | |
| 2009/0318962 A1 | 12/2009 | Spedden et al. | |
| 2011/0160749 A1 | 6/2011 | Gordon et al. | |

OTHER PUBLICATIONS

International Search Report and Written Opinion for corresponding PCT application No. PCT/US2011/036042, date of mailing Jan. 18, 2012.

Koob, Thomas J., Biomimetic approaches to tendon repair, Comparative Biochemistry and Physiology Part A 133 (2002) pp. 1171-1192.

* cited by examiner

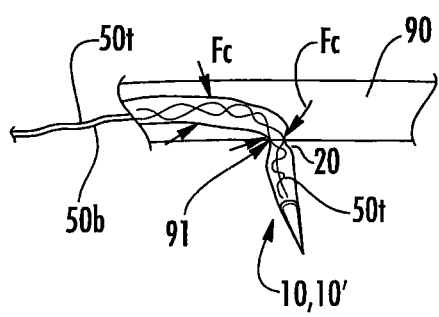 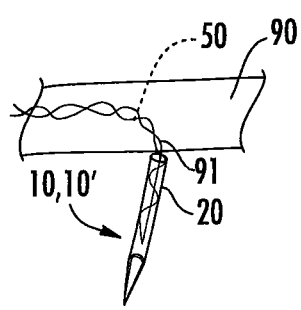 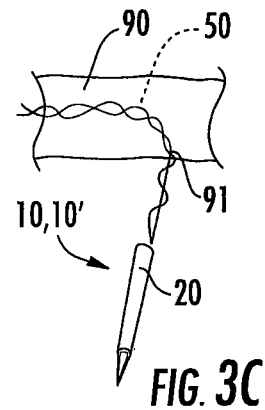
FIG. 3A     FIG. 3B     FIG. 3C
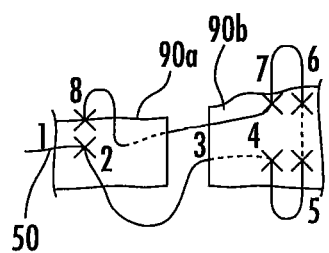 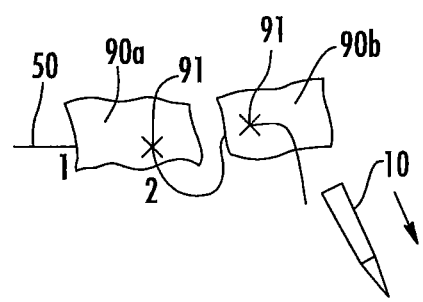
FIG. 3D     FIG. 3E

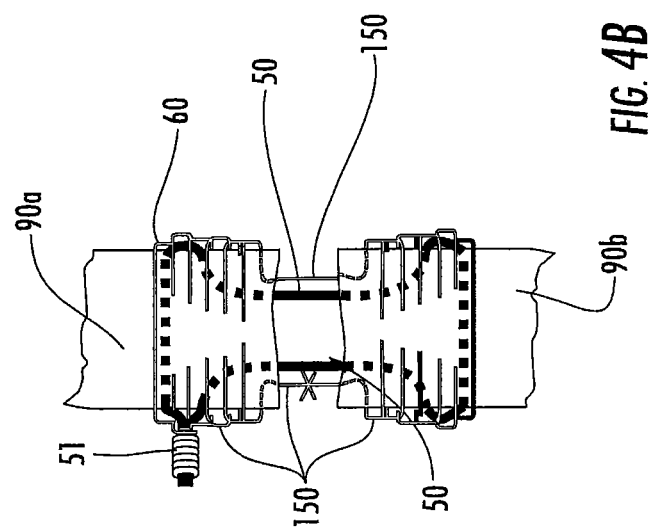
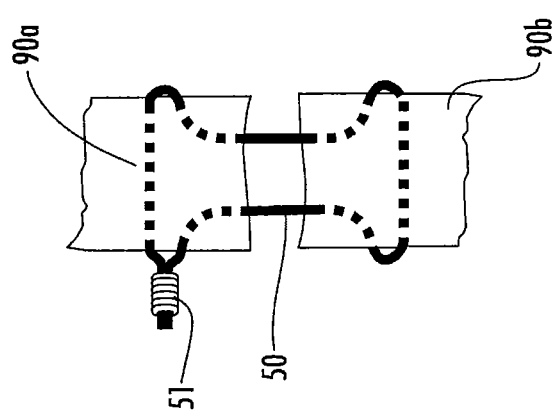
FIG. 4B
FIG. 4A

METHODS OF USING COMPRESSIBLE TUBES FOR PLACING IMPLANTS

RELATED APPLICATIONS

This application claims the benefit of and priority to U.S. Provisional Application Ser. No. 61/345,292, filed May 17, 2010, the contents of which are hereby incorporated by reference as if recited in full herein.

FIELD OF THE INVENTION

The invention relates to medical constructs.

BACKGROUND OF THE INVENTION

It is believed that the linear organization of natural collagen fibers in tendons results in optimal stiffness and strength at low strains under tensile loads. However, this organization makes repairing tissue such as ruptured or lacerated tendons difficult. Current suturing techniques to join split ends of tendons, while providing sufficient mechanical strength to prevent gapping, are often inadequate to carry normal loads and may not ever allow the tendon to regain its original mechanical properties or mobility. Immobilization protocols used to restore tendon congruity may result in scar formation at the repair site and peripheral adhesions that can limit excursions. One or more similar issues may be associated with conventional ligament repair techniques.

When placing certain soft-tissue type implants, such as for example, collagen fiber implants, the fibers can expand upon hydration, which can make it difficult to place the implants in a desired orientation and/or position in the body. Also, the collagen fibers may be somewhat fragile and subject to breakage when unprotected, such as when using hemostat clamps.

SUMMARY OF EMBODIMENTS OF THE INVENTION

Embodiments of the present invention are directed to medical devices with compressible tubes for placing medical constructs in the body.

Embodiments of the invention are directed to medical delivery devices that include a needle and a tube. The tube includes a first segment that is attached to the needle and a second compressible and substantially impermeable segment that increases in size relative to the first segment and extends rearward of the needle. The second segment defines an open elongate interior channel adapted to loosely hold at least about 30% of a length of a flexible medical implant therein.

The medical device can hold a flexible elongate medical implant with a length so that at least about 3 cm of the implant length is held in the compressible second segment interior channel. The medical implant can be slidably insertable into the second segment interior channel and can be loosely held inside the tube interior channel spaced apart from the needle during intrabody placement using the needle and tube.

In some embodiments, at least about 25%, typically at least about 30% of the length of the implant is held inside the compressible channel.

The flexible medical implant can be a partially hydrated or dry twisted or braided collagen fiber implant that is loosely held inside an outer wall of the tube second segment enclosing the interior channel.

The tube can have a forward end portion that resides in an interior chamber of a rearward portion of the needle.

The tube can be swaged to the needle and has a smooth transition segment from the needle to the tube to inhibit snagging when inserted through soft tissue during surgical use.

The tube can be attached to a drilled end needle.

The needle can have a length and the first segment of the compressible tubing can extend snugly against a portion of the needle, (e.g., 1 cm or more, typically at least about 30% of the length of the needle). The device can further include an elongate flexible braided or twisted collagen fiber implant with at least about 3 cm of its length held loosely in a substantially straight arrangement inside the second segment of the compressible tube.

The needle can be shank-less and have a constant diameter outer wall upstream from a tip portion thereof. An inner wall of the first segment of the tube can be affixed to the outer wall of the needle. The device can further include a dry or partially hydrated collagen fiber implant having a length that swells (increases fiber diameter or size when in the body), and the tube second segment can have a length that is sufficient to encase at least about 30% of the implant held therein.

The tube can be formed of heat-shrink tubing that is heated to shrink to conform and affix to at least about 1 cm (in some embodiments 30%) of an outer wall of the needle.

The medical implant can be a tendon or ligament repair implant having a suture with at least 3 cm of its length being held in the second segment of tube.

The medical implant held in the second segment of the tube can be a length of substantially or entirely dry or partially hydrated biocompatible collagen fibers twisted or braided together that swell when exposed to a local fluidic environment in situ.

The medical implant held in the second segment of the tube can include a plurality of long fibers derived from soluble collagen that are in a dry or partially hydrated state and arranged as parallel long fibers that are twisted and/or woven or braided together.

The fibers can include NDGA-polymerized collagen fibers.

The fibers can have a cross-sectional size, on average when dry, of between about 0.001 inches to about 0.2 inches (when dry, on average), wherein the implant has a number of strands of fibers that is between about 2-100, and wherein the number of fibers per strand is between about 2 to 1200.

The medical implant can be for a ligament or tendon repair.

The medical implant can be at least one of a suture or a cable that is configured to repair an acromioclavicular (AC) joint.

The tube can be configured so that compression of a portion of the second segment caused by contact with surrounding local structure during implantation into soft tissue temporarily compresses the tube to tightly hold the implant therein.

Other embodiments are directed to medical kits for a ligament or tendon repair. The kits include a delivery device having a flexible compressible substantially impermeable tube with an open interior attached to a needle having increased structural rigidity relative to the flexible tube; and a length of tendon or ligament repair or replacement material comprising dry or partially hydrated synthetic collagen fibers releasably held in the open interior of the tube or provided as a separate component for insertion into the open interior channel.

The repair or replacement material can be a twisted or braided construct of a plurality of collagen fibers. The delivery device and repair or replacement material are held in at least one sterile package.

Still other embodiments are directed to methods of placing a medical construct in the body of a subject. The methods include: (a) providing a surgical delivery device comprising a needle attached to a compressible tube with an open interior channel, the compressible tube surrounding an elongate medical construct having a body with a length, wherein at least about 3 cm of the construct body length is held in the open interior channel of the tube, wherein the construct body swells when exposed to liquid in the body of a subject; (b) pulling the needle and tube through local intrabody structure; (c) compressing the tube and the medical construct in response to pressure applied from contact with local structure during the pulling step, thereby also pulling the portion of the medical construct held in the tube through the local structure; then (d) separating the medical construct from the tube after the compressing step by continuing to pull the tube after the tube has exited the local structure so that the medical construct is loosely held in the tube, thereby removing the tube from the medical construct and placing the medical implant in the body.

The medical construct can include dry or partially hydrated fibers when held inside the tube that swell when hydrated in the body.

The medical construct can include a plurality of strands of biocompatible collagen fibers having at least a portion that is braided or twisted.

The method can further include inserting the needle in soft tissue before the pulling and compressing steps. The pulling can be carried out by pulling the needle and tube through the soft tissue. The compressing can be carried out so that the tube and the medical construct are compressed in response to pressure applied from contact with the soft tissue during the pulling step thereby also pulling the portion of the medical construct held in the tube through the soft tissue. The separating step can be carried out by continuing to pull the tube after the tube has exited the soft tissue so that the medical construct is loosely held in the tube thereby removing the tube from the medical construct and placing the medical implant in the body.

Yet other embodiments are directed to methods of assembling a medical delivery device with an implant for intrabody placement. The methods include: (a) providing a needle attached to a compressible tube having an open interior channel that extends a distance away from the needle; and (b) slidably inserting a medical implant comprising non-hydrated or partially hydrated braided and/or twisted collagen fibers into the open interior channel of the tube so that the implant is loosely held therein for intrabody placement using the needle and tube.

The implant can have a non-coated, non-tipped end, e.g., it may comprise a broomed end configuration.

The length of repair or replacement material can include a twisted or braided construct of a plurality of collagen fibers. The delivery device and repair or replacement material can be held in at least one sterile package.

The medical construct can include fibers that swell when hydrated in the body. The medical construct can include non-hydrated or partially hydrated strands of biocompatible collagen fibers having at least a portion that is braided or twisted.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Further features, advantages and details of the present invention will be appreciated by those of ordinary skill in the art from a reading of the figures and the detailed description of the embodiments that follow, such description being merely illustrative of the present invention.

BRIEF DESCRIPTION OF THE DRAWINGS

FIGS. 3A-3C are a top view of the delivery device shown in FIG. 2A shown in an exemplary use configuration according to some embodiments of the present invention.

FIGS. 3D and 3E are schematic illustrations of a delivery device that can be used to define multiple entry and exit points in local tissue according to embodiments of the present invention and/or to secure two adjacent pieces of tissue according to embodiments of the present invention.

FIG. 4A is a schematic illustration of a tendon repair procedure according to some embodiments of the present invention.

FIG. 4B is a schematic illustration of a tendon repair procedure similar to that shown in FIG. 4A but with an exemplary supplemental suture configuration according to some embodiments of the present invention.

DETAILED DESCRIPTION

Figure 1:
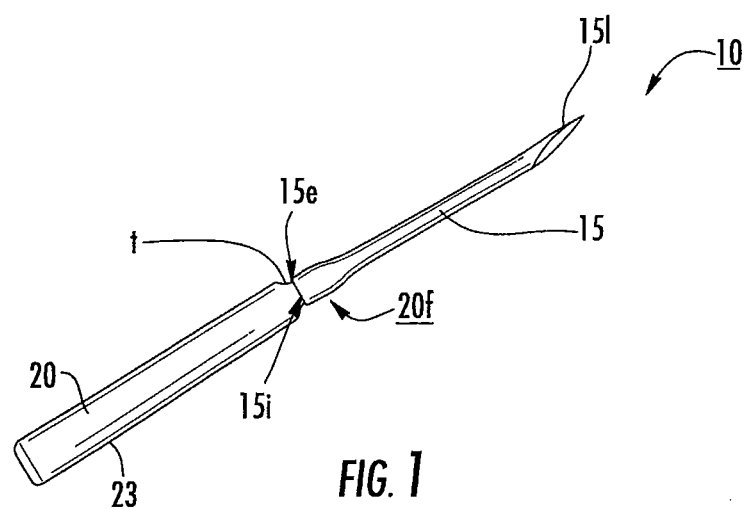
FIG. 1 is a side perspective view of a delivery device according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. In the figures, broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The terms "implant," "prosthesis" and "construct" are used interchangeably herein to designate an implantable medical product configured to repair or replace (at least a portion of) tissue, typically soft tissue, such as, for example, muscle, a natural tendon, ligament (e.g., ACL), AC joint, or other skin or tissue of a mammalian subject (for veterinary or medical (human) applications). The term "implantable" means the device can be inserted, embedded, grafted or otherwise chronically attached or placed on or in a patient.

The term "impermeable" with respect to the delivery system tube means that the device is resistant to liquid diffusion so as to inhibit undue swelling (e.g., hydration) of any implant or construct material held therein during placement of the construct in a mammalian body.

The term "needle" refers to a substantially rigid device that has a sharp leading end.

The term "loosely held" means that the medical implant material can be slidably inserted into the tube and resides in the tube in a use configuration with a low engagement force, e.g., the implant can be easily separated from the tube by pulling the end of the material not held by the tube or by pulling the needle end of the tube with a low tensile force while the material extending from the other end of the tube is held with a clamp or frictional engagement with local structure. The medical implant is not in snug abutting contact with an outer wall of the compressible tube.

The term "collagen fibers" refers to natural and synthetic collagen-derived fiber materials. Collagen "microfibrils," "fibrils," and "natural fibers" refer to naturally-occurring structures found in a tendon. Microfibrils are about 3.5 to 50 nm in diameter. Fibrils are about 50 nm to 50 µm in diameter. Natural fibers are above 50 µm in diameter. A "synthetic fiber" refers to any fiber-like material that has been formed and/or chemically or physically created or altered from its naturally-occurring state. For example, an extruded fiber of fibrils formed from a digested tendon is a synthetic fiber, but a tendon fiber newly harvested from a mammal is a natural fiber. Of course, synthetic collagen fibers can include non-collagenous components, such as particulates, hydroxyapatite and other mineral phases, or drugs that facilitate tissue growth. See, U.S. Pat. No. 6,821,530, hereby incorporated by reference herein. For example, the compositions can contain carbon nano-tubes, zinc nano-wires, nano-crystalline diamond or other nano-scale particulates, and larger crystalline and non-crystalline particulates such as calcium phosphate, calcium sulfate, and apatite minerals. For example, the fibers and/or constructs formed of the fibers can include compositions that contain therapeutic agents such as bisphosphonates, anti-inflammatory steroids, growth factors such as basic fibroblast growth factor, tumor growth factor beta, bone morphogenic proteins, platelet-derived growth factor, and insulin-like growth factors; chemotactic factors such fibronectin and hyaluronan; and extracellular matrix molecules such as aggrecan, biglycan, and decorin. In some embodiments, the fibers and/or constructs can contain cells, engineered cells, stem cells, and the like, as well as combinations of the above.

The term "flexible" means that the so-called member can be flexed or bent.

The terms "braided" and "woven" and derivatives thereof mean structures that are braided and/or (inter)woven, interlaced and/or interlocked in any manner, with a plurality, typically three or more, fibers or bundles of fibers together, including manually or automatically woven, braided, knitted and/or knotted and combinations of these or other interlocking or interlaced constructions. The woven constructs may comprise a plurality of warp and weft fibers. The fibers are typically collagen derived fibers.

The term "twisted" and derivatives thereof mean to entwine two or more strands of fibers, typically collagen derived fibers, into a single strand. The twisted configuration can be formed by serially turning the fibers/strands in a clockwise or counter clockwise direction to introduce a series of turns extending along a lengthwise direction, including manually or automatically twisting the fibers and/or fiber bundles. The strands can have a single fiber or multiple fibers.

The construct, typically formed or comprising long (e.g., between about 1 cm to about 1 m) synthetic collagen (derived from donor collagen fibrils) fibers, may have a substantially constant length, whether in the dry or partially hydrated configuration or the fully hydrated configuration but typically swell upon exposure to hydration relative to a size at a dehydrated or partially hydrated state as held inside the compressible tube during delivery.

The term "dry" or "dehydrated" means the construct fibers have a moisture content that is substantially less than the moisture amount that is present when fully hydrated. The term "partially hydrated" means that the construct and/or fibers thereof have a moisture content that is less than about 50%, typically less than about 75% of the moisture content at full hydration, measured ex vivo after 24 hours in a saline bath at ambient conditions.

Referring now to the figures, FIG. 1 shows an example of a medical delivery device 10. The device 10 includes a needle 15 and a flexible tube 20. The tube 20 may be optically transmissive (e.g., translucent or transparent) to allow a clinician to view the portion of the medical implant 50 held in the interior of the tube 20. The tube 20 may be impermeable to inhibit swelling (e.g., hydration) of the implant material during positioning of the implant 50 (FIG. 3A) in the body based on exposure to local conditions (body fluids) using the delivery device 10.

The needle 15 can have one or two open ends or closed ends. The needle 15 may have an open or closed leading end with the leading end 15/being sharp and relatively small for ease of insertion through local structure, such as, for example, soft tissue. The needle 15 may have a solid body or may have a hollow body (e.g., have a cannula configuration). The needle can be a drilled-end needle or fenestrated needle. The needle 15 can have an open proximal end 15e. The needle 15 may be formed from hypodermic tubing. The needle 15 may have a circular (cross-section) or other geometric configuration. The needle 15 may be a 12 gauge needle (e.g., have a forward end of about 0.08 inches or less, such as between about 0.04 to about 0.08 inches) and the tube 20 may be slightly larger. The needle 15 can have a constant size or may taper from a forward end to a distal and/or medial section. The needle 15 is typically shank-less, e.g., it does not require a smaller neck facing the implant in the tube 20, but may optionally have a shank. An example of needle with a shank that is snugly attached to a small tipped leading edge of a suture is shown in U.S. Pat. No. 5,259,845, the contents of which are hereby incorporated by reference as if recited in full herein.

The tube 20 can be attached to the needle 15 in any suitable manner. In the embodiment shown in FIG. 1, the tube 20 can be attached to the needle 15 by inserting a forward or leading edge portion of the tube 20$f$ into an interior 15$i$ of the (hollow or open end) needle 15. The two components 15, 20 can also be swaged together, similar to a suture needle. However, other attachment configurations may also be used, for example, adhesive attachment, ultrasonic bonding, crimping, heat shrink and the like. As shown, the attachment transition region "t" between the needle 15 and the larger tube 20 can be relatively smooth to facilitate ease of insertion (and anti-snagging) during use.

Figure 2A:
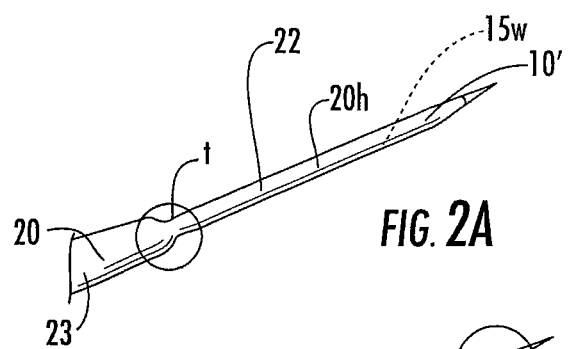
FIG. 2A is a side perspective view of another delivery device according to embodiments of the present invention.
Figure 2B:
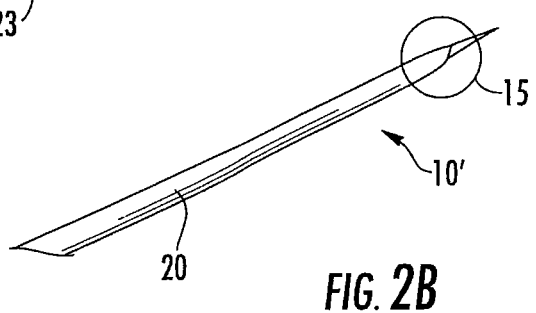
FIG. 2B is a side perspective view of the device shown in FIG. 2A before heat shrinking.

FIGS. 2A and 2B illustrate alternate embodiments of the delivery device 10'. As shown, the device 10' includes a tube 20 that can be attached to an exterior surface or wall of the needle 15$w$. In some embodiments, the tube 20 can be heat-shrink tubing that can be heated to shrink against and conformably attach to the outer wall of the needle 15$w$. The tube 20 can include a first segment 22 that snugly resides about the needle 15 and a larger elongate second segment 23 that defines an open channel and has a larger size that can loosely hold the implant for delivery and/or intrabody placement. Where the tube 20 is mounted to an exterior surface of the needle 15, the first segment 22 of the tube 20 can reside over at least a major portion of a length of the needle 15. In some embodiments, the needle 15 can have a length that is between at least 10-50% of the length of the second segment 23 of the tube extending rearward of the needle 15.

FIG. 2B illustrates the tube 20 before heat shrinking and FIG. 2A illustrates the tube 20 firmly attached to the needle 15 after heat shrinking. FIG. 2A illustrates that the tubing 20 can extend close to, e.g., adjacent, a forward/leading end of the needle 15 so that the tube 20 overlies at least a major portion of the length of the needle 15, with the heat shrink portion 20$h$ typically residing over between about 20% to about 95% of the length of the needle, and more typically between about 30-70% of the length of the needle.

In other embodiments, the tube 2Q can be configured to reside over a minor portion of the length of the needle and/or or a smaller length or portion of the tube 20 overlying the needle 15 may be heat-shrink attached to the needle 15, such as, for example, at least about 1 cm.

Figure 7:
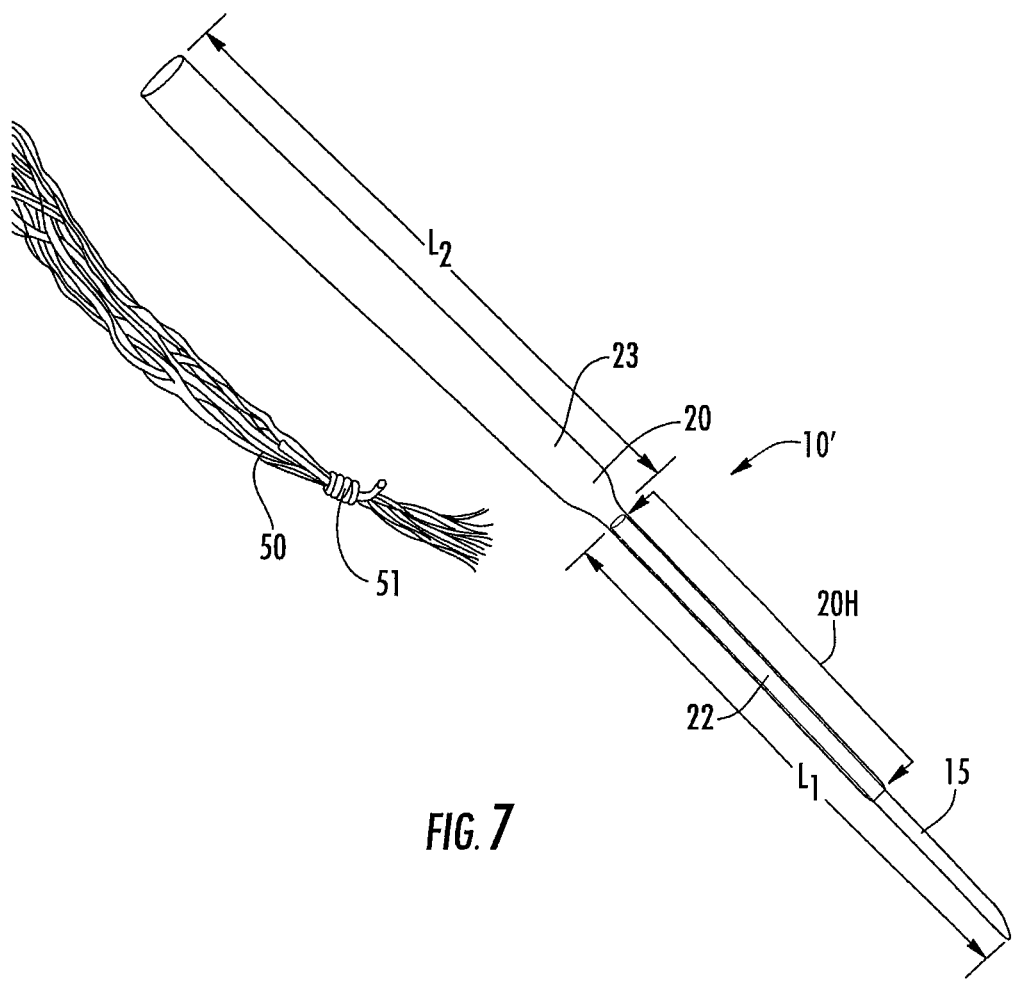
FIG. 7 is a side view of an exemplary delivery device adapted to hold a soft tissue implant according to embodiments of the present invention.
Figure 8:
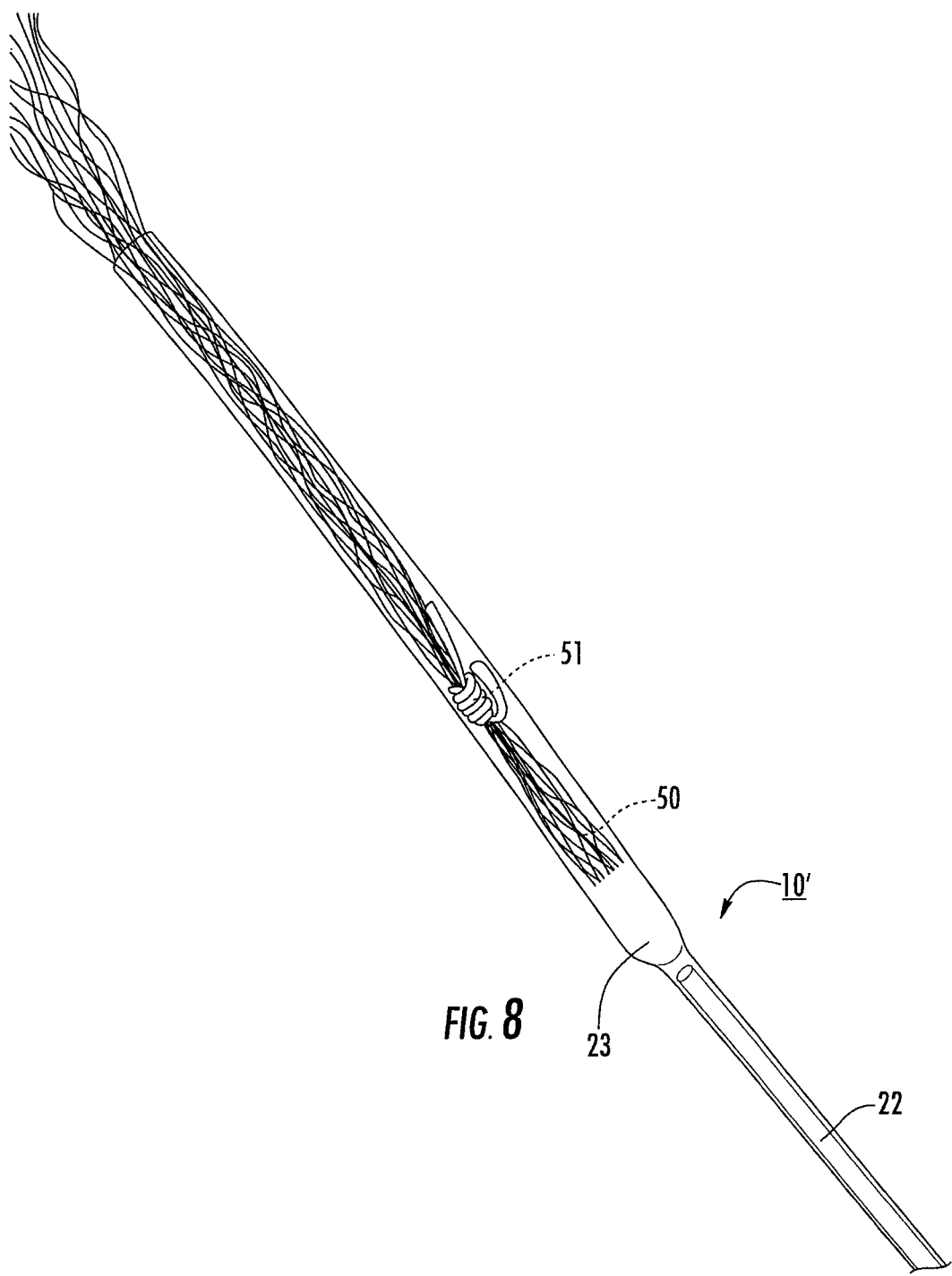
FIG. 8 is a side view of the delivery device enclosing a leading end of the implant shown in FIG. 7 according to embodiments of the present invention.

The needle 15 may have a length "L" (FIG. 2C) that is between about 70-100% of the length of the second segment 23 of the tube 20 (FIGS. 7, 8). In other embodiments, the needle 15 may have a shorter length than that shown, such as 30%, 20% or even 10% or less the length of the second segment 23. As before, the transition "t" between the end of the needle 15 and the larger tube 20 can be relatively smooth (a gradual increase in size). However, other larger, typically tapered, transitions can be used.

Figure 2C:
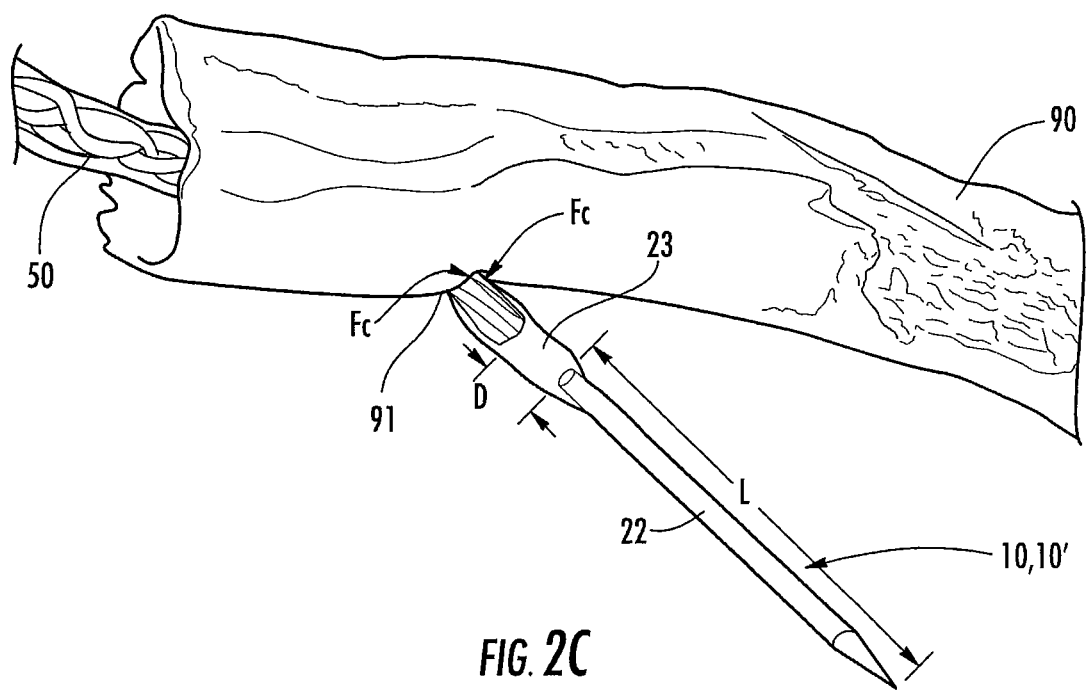
FIG. 2C is a top view of the delivery device shown in FIG. 2A shown in an exemplary use configuration according to some embodiments of the present invention.

The tube 20 can be configured to fit or accommodate the implant 50 and can, in some embodiments, loosely and releasably hold the implant 50 therein. As shown in FIG. 2C, the leading end of the implant 50 can reside a distance "D" spaced apart from the trailing end of the needle, so as to be in non-abutting (non-compressive contact) relationship with both outer wall of the tube thereat and the end of the needle. The tube 20 can, for example, have a diameter of between about 0.05 inches to about 0.5 inches, typically between about 0.1 to about 0.2 inches, for certain medical uses, such as, for example, soft tissue repairs, including tendon and/or ligament repairs. However, other dimensions and sizes may be used.

The tube 20 can have a length sufficient to define an open interior channel that can encase between about 20-100% of the implant 50 for delivery in the body, typically between about 30-70% of the length of the implant, including, for example about a leading half of the implant. The implant 50 can be provided in any desired length, typically between about 0.5 cm to about 50 cm, more typically between about 1 cm to 25 cm. In some embodiments, the implant 50 has a length between about 5 cm to about 25 cm, including between about and about 10 cm to about 15 cm or between about 15 to 20 cm. The implant 50 may have a width between about 0.05 to 8 cm, and is typically between about 1-3 cm. The implant 50 may have a thickness of between about 0.01 to about 30 mm, typically about 1-10 mm. The at least one suture 250 can extend at least about 1 inch off beyond each end of the ribbon body, typically between about 1-15 inches. The suture(s) 150 (where used) can be shorter on one end than the other (not shown). The implant 50 can include integrated sutures 250 that are woven into and extend over the entire length of the implant $L_3$ and beyond (see, e.g., FIG. 4C).

A common tube 20 and/or needle 15 size can be used to place a plurality of different size constructs because the implant 50 is typically loosely held in the tube 20. For example, a 12 gauge needle (a diameter of about 0.08 inches) with about a 0.0935 inch tube can be used to place a 108, 216 and 432 collagen fiber braid of various corresponding sizes. A more complete description of woven and braided collagen fiber constructs and methods of making same can be found in U.S. patent application Ser. No. 11/964,745, the contents of which are hereby incorporated by reference as if recited in full herein.

The tube 20 can be a thin polymeric material such as, for example, PTFE tubing. The term "thin" refers to tubing material that is between about 0.01 to about 0.0015 inches thick and may be even thinner. However, the tube 20 can include other polymers and/or be formed in other thicknesses. The tube 20 and/or needle 15 can be used with or without a lubricous biocompatible coating for ease of insertion. The biocompatible coating may also include therapeutic agents, such as anti-inflammatory and antibiotic materials. The term "polymer" refers to polymers, copolymers and derivatives and combinations thereof.

FIG. 3A illustrates the delivery device 10, 10' being used to place a construct 50 in soft tissue, such as a tendon. As shown, the device 10, 10' holds the elongate construct 50. FIG. 3A also illustrates that the construct 50 may be a braided (mesh) fiber construct.

FIG. 3A illustrates that a portion of the construct 50 is held and/or resides in the tube 20 and a portion of the construct 50 trails/extends outside of and behind the tube 20. The device 10, 10' can be used to pull the construct 50 through the soft tissue 90 out of an opening 91 formed by the needle 15. As the tube 20 passes through the local structure 90, e.g., surrounding structure (e.g., surrounding tissue) applies a compressive force "Fc" to the body of the tube 20 thereby firmly grasping the implant material 50 therein. After the tube 20 exits the local structure, e.g., soft tissue 90, the compressive forces Fc (e.g., pressure) on the tube 20 automatically abate, e.g., stop. The device 10, 10' and implant 50 can be easily disconnected when the tube is pulled after it exits the local structure 90.

FIGS. 3A-3C illustrate a sequence of steps (steps 1-3) that can be used to place the implant 50. FIGS. 3A-3C also illustrate that the implant 50 can be a twisted implant 50*t* or braided implant 50*b* of fibers, such as, for example, twisted or braided long (typically at least 2 inches long) collagen fibers that are held in the tube 20 in a partially or totally dehydrated state, and that, when placed in the body swell upon hydration. The implant 50 can be planar or tubular. For a more complete description of suitable twisted collagen fibers and methods of making same, see, U.S. patent application Ser. No. 12/465,433, the contents of which are hereby incorporated by reference as if recited in full herein.

Step 1 (see FIG. 3A) shows the device 10, 10' with the tube 20 compressed by local structure to grasp the implant 50*t*. Step 2 (see FIG. 3B) illustrates the tube 20 exiting the local structure (e.g., soft tissue) via exit port 91 created by the needle 15 thereby removing the compressive force that held the implant 50*t*. Step 3 (see FIG. 3C) shows that the device 10, 10' can be easily separated from the implant 50 by pulling the device 10, 10' which, without the compressive forces applied by the surrounding tissue, allows the device 10, 10' to be removed from the implant 50*t* while the implant remains in the target tissue 90 with a portion extending through port 91.

FIGS. 3D-3E illustrate that the delivery device 10, 10' can be used to make multiple entries and exits from local tissue, such as in two adjacent pieces of soft tissue 90*a*, 90*b* (e.g., created by a torn ligament or tendon) before releasing the delivery device 10, 10' from the implant material 50.

FIG. 3D illustrates that the delivery device 10, 10' can be used to penetrate local tissue in multiple entry and exit positions (labeled as locations "1"-"8") and position the implant 50 to extend between the two pieces of local tissue 90*a*, 90*b* (such as a torn ligament or tendon) and be secured to both pieces. FIG. 3E illustrates an alternate example of entry and exit positions.

Figure 4C:
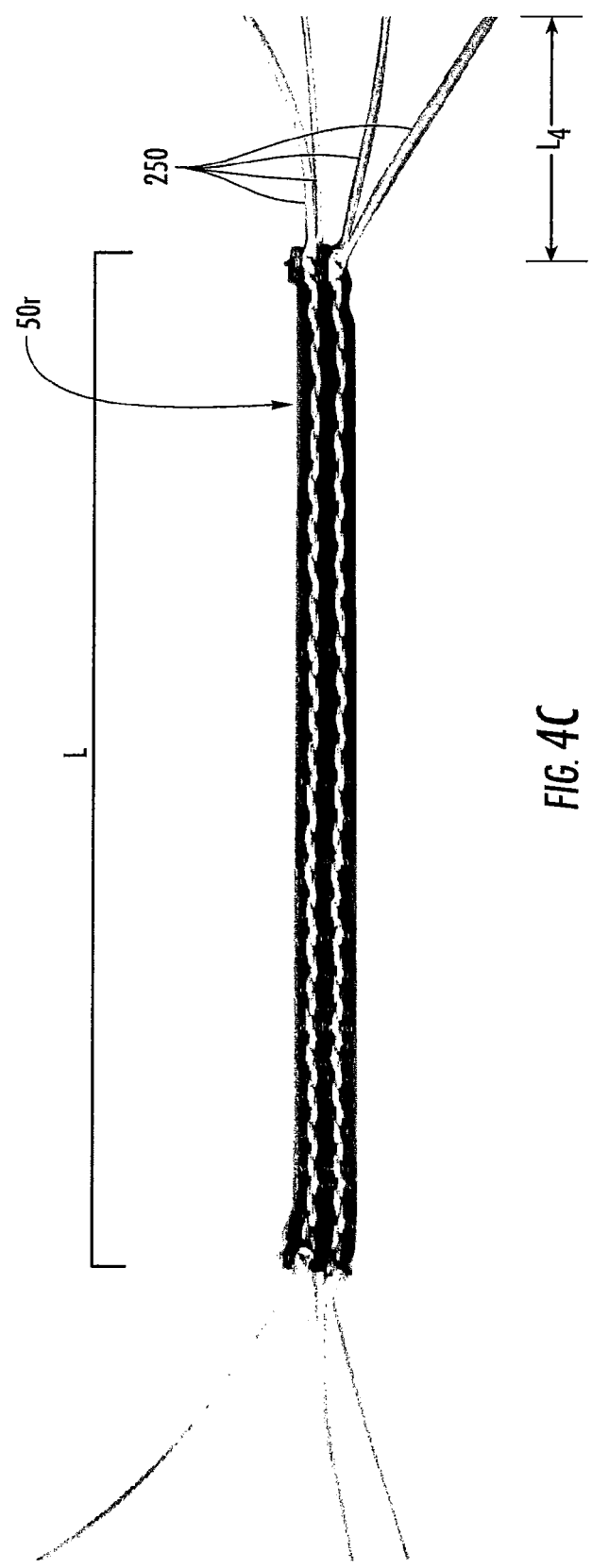
FIG. 4C shows an alternate embodiment of a collagen fiber ribbon implant that can be placed using the delivery devices according to some embodiments of the present invention.

FIG. 4A illustrates an example of a tendon repair with the implant material 50 in position based on the use of the delivery device 10, 10'. As shown, the implant 50 can include a fixation knot 51, such as a nail knot defined by loops of a suture (such as a six loop nail knot). The knot 51 can be held in the tube 20 during delivery/implantation using the delivery device 10, 10'. FIG. 4B illustrates the implant 50 shown in FIG. 4A with a supplemental suture 150. The supplemental suture 150 can be a #2 TiCron suture configured with Krackow stitches, such as about 6 on each side of the tear 90*a*, 90*b* to help stabilize the implant 50 in position and/or provide additional structural support at least during an initial healing period post surgery. However, the delivery device 10, 10' can also be used to place other implants. As shown in FIG. 4C, the delivery device may be configured to hold and deliver braided ribbons 50*r* with at least one integrated suture 250 that extends over the entire length of the implant $L_3$ and out from each end a distance $L_4$. The extension length $L_4$ can be between 1-500 mm or even greater, but is typically between about 20-400 mm. For additional description of collagen fiber ribbons with integrated sutures, see co-pending, co-assigned, U.S. Provisional Application Ser. No. 61/450,179, the contents of which are hereby incorporated by reference as if recited in full herein.

Also, the construct 50 can optionally include, e.g., be coated, impregnated and/or amalgamated with, a gel or other material. The coating may be to promote fibroblasts, and/or comprise one or more of an anti-inflammatory agent, an antibiotic or other therapeutic agent. The construct 50 can be absorbed, resorbed and/or biodegradable over time. In some embodiments, the constructs 50 can be configured to have similar or greater tensile strength, stiffness and dynamic flexibility as corresponding natural tissue, e.g., natural ligament or tendon fibers. Embodiments of the invention may be particularly suitable for augmenting, repairing or replacing tendons and ligaments.

In some embodiments, the fibers comprise collagen fibers formed in any suitable manner to be acceptable as a biomedical implant/construct.

As noted above, in particular embodiments, the fibers can comprise NDGA-treated collagen. Suitable ways of forming NDGA-polymerized and/or -treated fibers are described in U.S. Pat. Nos. 6,565,960 and 6,821,530, the contents of which are hereby incorporated by reference as if recited in full herein. Generally stated, bulk collagen can be solubilized by digestion with a protease, then extruded into a synthetic fiber. Properly processed NDGA polymerized fibers are biocompatible. After the polymerization process, the fibers can be washed in ethanol and phosphate buffered saline to remove cytotoxins due to leachable reaction products.

NDGA-treated collagen fibers are biocompatible and have desirable mechanical properties. For additional discussion of the NDGA polymerized fibers, see, Thomas J. Koob, *Biomimetic approaches to Tendon Repair*, Comparative Biochemistry and Physiology Part A 133 (2002) 1171-1192.

In some embodiments, the collagen fibers may be high-strength. The term "high-strength" refers to fibers having an average tensile strength of at least about 150 MPa, such as between about 180 MPa and 350 MPa, and typically, for bovine-, porcine- or caprine-based "donor" collagen, between about 180 MPa and 280 MPa, such as between about 240-279 MPa (measured on average). The fibers may also have suitable stiffness and strain yield. In general, the fibers can have a stiffness of at least about 200 MPa (e.g., at least about 300, 400, 500, or 600 MPa), and a strain at failure of less than about 20% (e.g., less than about 15 or 10%).

In particular embodiments, the fibers may be formed with a relatively thin diameter, such as, for example about a 0.07 mm dry diameter (on average) and about a 0.09 mm wet diameter (on average) or a dry diameter on average of about 0.08 mm and a wet diameter on average of about 0.13 mm. However, other sizes may be used.

To make the collagen fibers, preparatory donor collagen material can be pepsin-derived or solubilized collagen that is processed/purified. The purified collagen preparatory material is dialyzed a plurality of times in a selected liquid for a desired period of time. The dialyzing is typically repeated three times. The dialyzing can be carried out against dionized (DI) water in a volume ratio of between about 30:1 to about 100:1, typically about 60:1, for between about 30-90 minutes, typically about 40 minutes. The dialyzing can form a substantially clear gel of collagen fibrils indicating good organization (substantially parallel fibrils), where opacity indicates less organization. The organization can help improve tensile strength of subsequently cross-linked fibers.

The dialyzed collagen material can be incubated for a desired time before placing in a fiber-forming buffer. The dialyzed gel can be cross-linked to provide collagen fibers for medical constructs. The polymerization (e.g., cross-linking) can be carried out using NDGA or other suitable cross-linking agent and the resultant collagen fibers can be relatively thin, such as, for example, about 0.08 mm dry diameter (on average).

The incubation may be for at least about 24 hours, typically 24-48 hours, and may be at room temperature of between about 15-30° C., typically about 25° C. The dialysis process can be used before cross-linking for subsequent use with any suitable cross-linking materials, such as, for example, to promote collagen organization, and the process is not limited to NDGA, but may be useful with other materials, including, for example, glutaraldehyde. For additional discussion of methods used to form high-strength NDGA treated collagen fibers, see, U.S. patent application Ser. No. 11/964,756, the contents of which are hereby incorporated by reference as if recited in full herein.

The implants 50 can include swellable collagen fibers that have a cross-sectional size, on average, when dry, of between about 0.001 inches to about 0.2 inches. The implant can include a number of strands of collagen-derived fibers such as between about 2-100, and the number of fibers per strand can be between about 2 to 1200.

In some embodiments, the implant 50 may have between about 1-1000 yarns, typically between about 3-100 yarns some of which are weft and some of which are warp yarns.

The implant 50 can be configured to have substantially the same physical thickness and/or configuration as the replaced or repaired tissue so as to not cause discomfort or physical abnormalities in structure.

As desired, the body of the implant 50 can include a smooth outer sheath that may be formed by a coating, gel or other material. In particular embodiments, the implant 50 can comprise polyglycolic acid, polylactic acid, or combinations of these or other substances.

Figure 5:
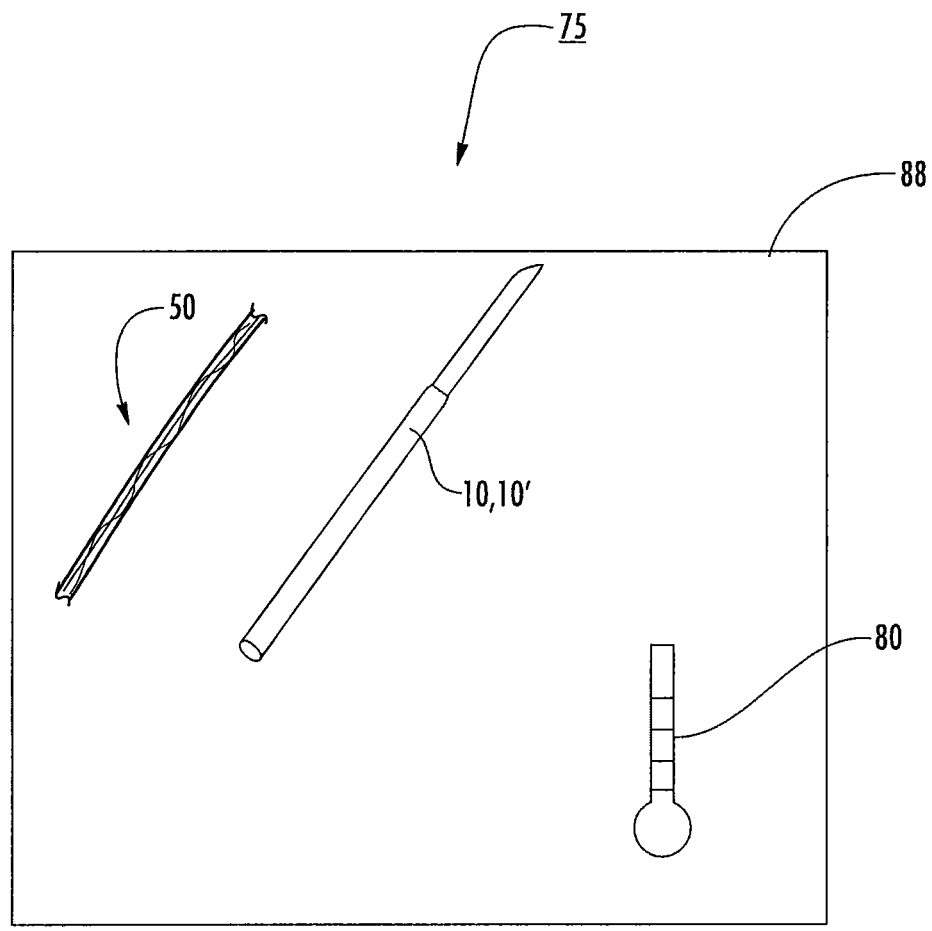
FIG. 5 is a schematic illustration of a medical kit according to embodiments of the present invention.

FIG. 5 illustrates a medical kit 75 that includes the delivery device 10, 10' and optionally, at least one construct 50, in a sealed package 88. The construct 50 may be held dehydrated or partially hydrated in the package 88 or in another separate package (not shown). The kit 75 may include a temperature warning so that the construct 50 is not exposed to unduly hot temperatures that may degrade the implant. A temperature sensor 80 may optionally be included on or in the package 88 of the kit 75 to provide a visual or audible alert to a clinician as to any excessive or undue temperature exposure prior to implantation. The construct 50 can be held in the tube 20 in the package 88. The construct 50 can be inserted into the tube 20 of the device 10, 10' by the clinician in situ. This may also allow the clinician to select the desired construct 50 from constructs 50 in a range of sizes that may be part of the package 88 or provided as separate content. The delivery device 10, 10' can be a "universal" delivery device that is configured to accommodate soft tissue implants in a range of sizes.

Figure 6:
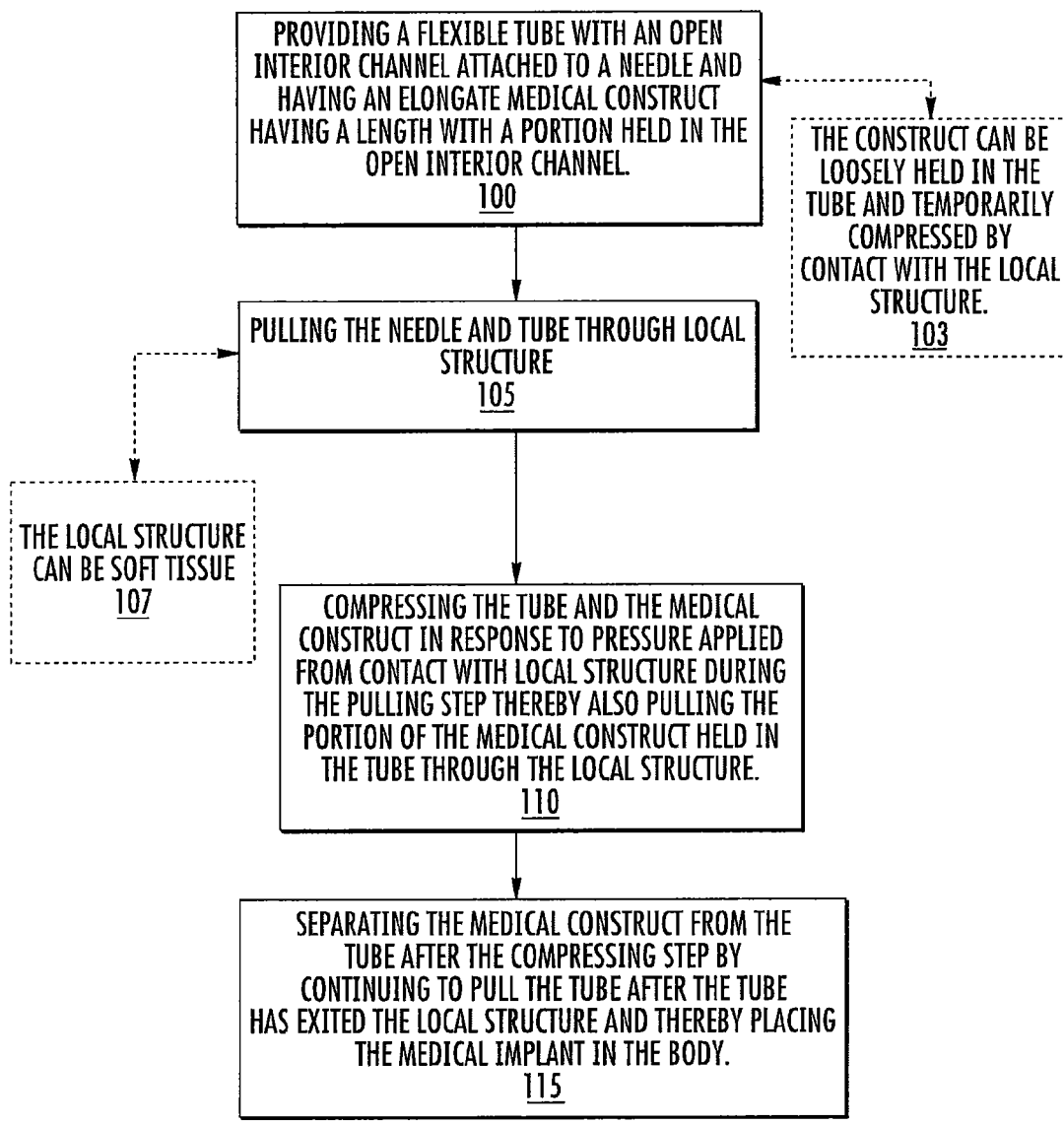
FIG. 6 is a flow chart of exemplary operations that can be used to carry out methods according to some embodiments of the present invention.

FIG. 6 is a flow diagram of exemplary operations that can be used to carry out embodiments of the present invention. A flexible tube with an open interior channel attached to a needle and having an elongate medical construct having a length with a portion held in the open interior channel is provided (block 100). The needle and tube are pulled through local structure (block 105). The tube and the medical construct are compressed in response to pressure applied from contact with local structure during the pulling step, thereby also pulling the portion of the medical construct held in the tube through the local structure (block 110). The medical construct is then separated from the tube after the compressing step by continuing to pull the tube after the tube has exited the local structure so that the medical construct is loosely held in the tube, thereby removing the tube from the medical construct and placing the medical implant in the body (block 115).

The local structure can optionally be soft tissue (block 107). The construct can optionally be loosely held in the tube and temporarily compressed by contact with the local structure (block 103).

Although described herein primarily with respect to collagen-derived fiber implants, it is contemplated that the delivery devices 10, 10' can deliver other types of implants.

The present invention is explained in greater detail in the following non-limiting Examples.

EXAMPLES

FIGS. 7 and 8 show a delivery device 10' with the tube 20 as a heat shrink tube and with the medical construct 50 formed with braided NDGA-collagen fibers. FIG. 7 illustrates that the heat shrink portion 20*h* extends over more than half of the length of the needle 15 and that the second segment of the tube 23 has a length that is between about 60-100% that of the needle 15. As shown, the second segment 23 has a longer length $L_2$ than the length $L_1$ of the needle 15.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A method of placing a medical construct in a body of a subject, comprising:
   providing a surgical delivery device comprising a needle attached to a compressible tube with an open interior channel having an open trailing end residing a distance away from the needle, the compressible tube surrounding an elongate medical construct having a body with a length and having a free leading end in the tube, wherein at least 20% of the construct body length, including the leading free end, is releasably held in the open interior channel of the tube, wherein the construct body swells when exposed to liquid in the body of the subject;
   pulling the needle and tube through a local intrabody structure;
   compressing the tube and the medical construct in response to pressure applied from contact with the local intrabody structure during the pulling step, thereby also pulling the portion of the medical construct held in the tube through the local intrabody structure as the tube is pulled through the local intrabody structure; and
   only securing the medical construct to the tube and needle using a compression force that is temporarily applied during the compressing step; then
   separating the medical construct from the tube after the compressing step by continuing to pull the tube after the tube has exited the local intrabody structure so that the medical construct entirely slidably exits the open trailing end of the tube and placing the medical construct in the body of the subject.

2. A method according to claim 1, wherein the medical construct comprises dry or partially hydrated fibers when held inside the tube that swell when hydrated in the body of the subject, and wherein the medical construct is loosely held in the tube when the tube is in an uncompressed state, wherein the tube is impermeable and has a first segment that is fixedly attached to the needle and a second segment with a greater diameter that extends rearward of the needle such that a maximum diameter of the second segment is greater than a maximum diameter of the first segment and the needle, wherein the leading free end of the medical implant is not directly or indirectly attached to the needle or tube when the tube is in the uncompressed state.

3. A method according to claim 1, wherein the medical construct comprises a plurality of strands of biocompatible collagen fibers having at least a portion that is braided or twisted, and wherein the medical construct further comprises at least one fixation knot residing in the tube in the providing step.

4. A method according to claim 1, further comprising inserting the needle in soft tissue before the pulling and compressing steps, wherein the pulling comprises pulling the needle and tube through the soft tissue, wherein the compressing is carried out so that the tube and the medical construct are compressed in response to pressure applied from contact with the soft tissue during the pulling step thereby also pulling the portion of the medical construct held in the tube through the soft tissue; and wherein the separating step is carried out by continuing to pull the tube after the tube has exited the soft tissue so that the medical construct is loosely held in the tube thereby placing the medical construct in the body of the subject.

5. A method according to claim 1, wherein the tube has an end portion that is fixedly attached to the needle, and wherein the compressible tube has an elongate body which is flexible and impermeable and that increases in diameter relative to the end portion attached to the needle, and wherein the separating step is carried out by pulling the needle and compressible tube out of the body of the subject while the elongate medical construct exits the open trailing end to thereby place the medical construct in the body of the subject.

6. A method according to claim 1, wherein the medical construct has an opposing trailing end, wherein the free leading end is held as a free end inside the tube spaced apart a distance from a trailing end of the needle, wherein the free leading end is not directly or indirectly attached to the tube or any needle.

7. A method according to claim 1, wherein the elongate medical construct is flexible and is releasably and loosely held inside the tube during the providing step, and wherein the separating step is carried out by the medical construct slidably exiting the open trailing end of the tube when the medical construct is disposed within soft tissue of the local intrabody structure while the needle and the tube are pulled out of and away from the soft tissue.

8. A method according to claim 1, wherein the tube is configured so that during the compressing caused by contact with soft tissue of the local intrabody structure during implantation temporarily compresses the tube such that only this compression tightly holds the medical construct inside the tube.

9. A method according to claim 1, wherein the medical construct has a length held in the interior channel of the tube that is at least 3 cm and/or is at least 30% of the construct length, and wherein the providing step is carried out to slidably insert the medical construct into the open interior channel to be loosely held inside the open interior channel.

10. A method according to claim 1, wherein the tube has a forward end portion that resides in an interior chamber of a rearward portion of the needle.

11. A method according to claim 1, wherein the tube is swaged to the needle and has a smooth transition segment from the needle to the tube to inhibit snagging when inserted through soft tissue during surgical use.

12. A method according to claim 1, wherein the needle is shank-less and has a constant diameter outer wall upstream from a tip portion thereof, and wherein an inner wall of a first segment of the tube is affixed to the outer wall of the needle, and wherein the medical construct is a flexible medical implant that comprises a dry or partially hydrated collagen fiber implant.

13. A method according to claim 1, wherein the tube is heat-shrink tubing that is heated to shrink to conform and affix to an outer wall of the needle, and wherein the compressible tube holds at least 40% of the construct body length therein.

14. A method according to claim 1, wherein the medical construct in the interior channel of the tube is a length of dry or partially hydrated biocompatible collagen fibers twisted, woven or braided together that swell when exposed to a local fluidic environment in situ.

15. A method according to claim 1, wherein the method further comprises placing the medical construct in soft tissue of the body of the subject as a ligament repair device.

16. A method according to claim 1, wherein the method further comprises placing the medical construct in soft tissue of the body of the subject as a tendon repair device.

17. A method according to claim 1, wherein the method further comprises placing the medical construct in soft tissue of the body of the subject as at least one of a suture or a cable that is configured to repair an acromioclavicular (AC) joint.

18. The method of claim 1, wherein the medical construct is a flexible medical implant that, during the providing step, is held inside the tube interior channel so that the free leading end of the flexible medical implant is spaced apart from a trailing end of the needle to not contact the needle and wall of the tube encasing the interior channel between the trailing end of the needle and the free leading end of the flexible implant.

19. A method of placing a flexible medical implant in a body of a subject, comprising:
providing a surgical delivery device comprising a needle attached to a compressible tube with an open interior channel having an open trailing end residing a distance away from the needle, the compressible tube surrounding an elongate flexible medical implant having a body with a length and having a free leading end in the tube with the free leading end held inside the open interior channel so that the free leading end of the medical implant is detached from and longitudinally spaced rearward of a trailing end of the needle, wherein at least 30% of the body length of the medical implant, including the leading free end, is releasably and loosely held in the open interior channel of the tube when the tube is in an uncompressed state, and wherein the implant body swells when exposed to liquid in the body of the subject;
inserting and pulling the needle and tube through intrabody soft tissue at least one time while the medical implant is held in the tube;
compressing the tube and the medical implant in response to pressure applied from contact with the soft tissue during the inserting and pulling steps, thereby also inserting and pulling the medical implant held in the tube through the soft tissue, wherein the compression of the tube and medical implant in response to contact with the soft tissue temporarily applies a compression force that by itself secures the medical implant in the tube during the inserting and pulling steps; then
pulling the tube away from the soft tissue while the medical implant entirely slidably exits the open trailing end of the tube thereby placing the medical implant in the body of the subject.

20. The method of claim 19, wherein the inserting and pulling steps are repeated in two separate pieces of soft tissue to connect the two pieces of soft tissue using the medical implant.

21. The method of claim 19, wherein the medial implant comprises a fixation knot which is held inside the tube in the providing step.

22. The method of claim 19, wherein the tube is impermeable and has a first segment that is fixedly attached to the needle and a second segment with a greater diameter that extends rearward of the needle such that a maximum diameter of the second segment is greater than a maximum diameter of the first segment and the needle, wherein the free leading end of the medical implant is not directly or indirectly attached to the needle or tube when the tube is in the uncompressed state.

23. The method of claim 19, wherein the inserting and pulling the tube through the intrabody soft tissue is carried out a plurality of times at laterally spaced apart and longitudinally spaced apart points of entry before then pulling the tube away.

24. A method of placing a flexible medical implant in a body of a subject, comprising:
providing a surgical delivery device comprising a needle attached to a compressible tube with an open interior channel having an open trailing end residing a distance away from the needle, the compressible tube surrounding an elongate flexible medical implant having a body with a length, at least one fixation knot, and a free leading end, wherein at least 30% of the body length of the medical implant, including the free leading end and the at least one fixation knot, is releasably held in the open interior channel of the tube when the tube is in an uncompressed state, and wherein the implant body swells when exposed to liquid in the body of the subject;
inserting and pulling the needle and tube through a local intrabody target anatomical structure at least one time while the medical implant is held in the tube;
compressing the tube and the medical implant in response to pressure applied from contact with the local intrabody target anatomical structure during the inserting and pulling steps, thereby also inserting and pulling the medical implant held in the tube through the local intrabody target anatomical structure, wherein the compression of the tube and medical implant in response to contact with the local intrabody target anatomical structure temporarily applies a compression force that by itself secures the medical implant in the tube during the inserting and pulling steps; then
pulling the tube away from the local intrabody target anatomical structure while the medical implant entirely slidably exits the open trailing end of the tube thereby placing the medical implant in the body of the subject.

* * * * *

UNITED STATES PATENT AND TRADEMARK OFFICE
CERTIFICATE OF CORRECTION

PATENT NO. : 9,610,151 B2  
APPLICATION NO. : 14/644739  
DATED : April 4, 2017  
INVENTOR(S) : Niu et al.

Page 1 of 1

It is certified that error appears in the above-identified patent and that said Letters Patent is hereby corrected as shown below:

In the Specification

Column 7, Line 36: Please correct "leading end 15/being sharp" to read -- leading end 15*l* being sharp --

Signed and Sealed this  
Fourteenth Day of November, 2017

Joseph Matal  
*Performing the Functions and Duties of the*  
*Under Secretary of Commerce for Intellectual Property and*  
*Director of the United States Patent and Trademark Office*